US011450193B2

(12) United States Patent
Bolduc et al.

(10) Patent No.: US 11,450,193 B2
(45) Date of Patent: Sep. 20, 2022

(54) HOSPITAL BED HEIGHT LIMITING SYSTEM

(71) Applicant: UMANO MEDICAL INC., L'Islet (CA)

(72) Inventors: Steve Bolduc, Beaumont (CA); Etienne St-Pierre, Quebec (CA); David Moreno, Quebec (CA); Gabriel Mercier, Saint-Vallier (CA); Esther Berthelot, Levis (CA)

(73) Assignee: UMANO MEDICAL INC., L'Islet (CA)

( * ) Notice: Subject to any disclaimer, the term of this patent is extended or adjusted under 35 U.S.C. 154(b) by 0 days.

(21) Appl. No.: 17/204,436

(22) Filed: Mar. 17, 2021

(65) Prior Publication Data

US 2021/0201647 A1 Jul. 1, 2021

Related U.S. Application Data

(60) Continuation of application No. 16/681,808, filed on Nov. 12, 2019, now Pat. No. 10,984,647, which is a division of application No. 15/818,248, filed on Nov. 20, 2017, now Pat. No. 10,497,247.

(51) Int. Cl.
| G08B 23/00 | (2006.01) |
| G08B 21/04 | (2006.01) |
| A61G 7/05 | (2006.01) |
| G16H 40/63 | (2018.01) |
| G08B 21/22 | (2006.01) |
| A61G 7/005 | (2006.01) |

(52) U.S. Cl.
CPC ........... *G08B 21/0461* (2013.01); *A61G 7/05* (2013.01); *A61G 7/0527* (2016.11); *G08B 21/22* (2013.01); *G16H 40/63* (2018.01); *A61G 7/005* (2013.01); *A61G 2203/20* (2013.01); *A61G 2203/30* (2013.01); *A61G 2203/44* (2013.01)

(58) Field of Classification Search
CPC ...... G08B 21/0461; G08B 21/22; A61G 7/05; A61G 7/0527; A61G 7/005; A61G 2203/20; G16H 40/63
USPC ...................................................... 340/573.4
See application file for complete search history.

(56) References Cited

U.S. PATENT DOCUMENTS

| 4,015,677 | A | 4/1977 | Silva |
| 5,276,432 | A | 1/1994 | Travis |
| 6,067,019 | A | 5/2000 | Scott |
| 6,208,250 | B1 | 3/2001 | Dixon et al. |
| 6,791,460 | B2 | 9/2004 | Dixon et al. |
| 6,897,781 | B2 | 5/2005 | Cooper et al. |

(Continued)

*Primary Examiner* — Tai T Nguyen
(74) *Attorney, Agent, or Firm* — Steptoe & Johnson LLP; Scott M. Richey

(57) ABSTRACT

A hospital bed height limiting system comprising a processing unit operatively connected to each of a user interface, an elevation mechanism of the hospital bed and a height sensor. The processing unit is operable to receive a minimum height via the user interface and receive from the height sensor a current elevation mechanism height. The processing unit is operable to determine the bed height based on the current elevation mechanism height, and in response to the bed height being equal to the minimum height, the processing unit is operable to cause the elevation mechanism to stop a downward movement of the elevation mechanism. A hospital bed comprising the hospital bed height limiting system is also provided.

20 Claims, 13 Drawing Sheets

(56) References Cited

U.S. PATENT DOCUMENTS

| | | |
|---|---|---|
| 7,253,366 B2 | 8/2007 | Bhai |
| 7,656,299 B2 | 2/2010 | Gentry |
| 8,123,685 B2 | 2/2012 | Brauers |
| 9,754,476 B2 | 9/2017 | Lemire et al. |
| 2004/0189475 A1 | 9/2004 | Cooper et al. |
| 2007/0157385 A1 | 7/2007 | Lemire |
| 2008/0169931 A1 | 7/2008 | Gentry |
| 2008/0275349 A1 | 11/2008 | Halperin et al. |
| 2013/0247300 A1 | 9/2013 | Menke |
| 2015/0000035 A1* | 1/2015 | Becker ................. A61G 7/0524 5/617 |
| 2016/0022218 A1 | 1/2016 | Hayes |
| 2016/0067127 A1 | 3/2016 | Shimada |
| 2016/0106345 A1 | 4/2016 | Kostic |
| 2016/0125716 A1 | 5/2016 | Ribble |
| 2016/0310045 A1 | 10/2016 | Hoffman |
| 2017/0143566 A1* | 5/2017 | Elku .................... A61G 7/0506 |

\* cited by examiner ion application of
U.S. patent application Ser. No. 16/681,808 filed on Nov. 12,
2019, now issued U.S. Pat. No. 10,984,647, which is a
divisional application of U.S. patent application Ser. No.
15/818,248 filed on Nov. 20, 2017 now U.S. Pat. No.
10,497,247 which are hereby incorporated by reference.

TECHNICAL FIELD

The present relates to hospital beds, and more specifically to patient exit detection methods and systems for hospital beds. The present also relates to methods and systems for limiting a height of a hospital bed, and to methods and systems for recalibrating a tare weight condition of a hospital bed.

BACKGROUND

Hospital beds and long term care beds are adapted to receive patients and to allow caregivers to monitor the patient and provide care to the patient.

Some hospital beds are provided with a system which detects a patient exiting the bed and which issues an alarm in response to alert a caregiver near the bed or remote from the bed. In some cases, the patient exit from the bed could be detected when the patient moves within a certain distance of the sides of the bed's deck.

Unfortunately, this system has a number of limitations. For example, if a bed exit alarm is triggered and the alarm is then deactivated while the patient is still in a location on the bed which indicates a possible bed exit, the bed exit alarm could be immediately be reactivated, therefore requiring the caregiver to once again deactivate the alarm.

Moreover, when the caregiver wishes to provide care to a patient, he/she will usually disable the bed exit alarm to be able to move the patient on the bed without running the risk of activating the alarm. Unfortunately, the caregiver may forget to re-arm the system once the patient has been tended to.

Hospital beds also sometimes include an integrated weight sensor or scale to measure a weight of a patient on the bed while allowing the patient to remain on the bed. It will be appreciated that hospital beds are often provided with medical equipment which can vary from patient to patient and which has a certain weight. To obtain a precise measurement of the patient's weight, an initial tare weight condition is therefore measured without the patient in the bed, and the initial condition correspond to a "zero" to which the measured parameters will be compared. The initial tare weight condition may comprise a weight measurement from the weight sensor. Once the patient is received on the bed, the patient's weight will therefore correspond to the difference between the measured weight and the In hospital beds provided with a patient location sensor, the initial tare weight conditions may also comprise a location measurement from the patient location sensor.

Unfortunately, the caregiver operating the hospital bed may mistakenly cause the system to perform a measurement of the initial tare weight condition while the patient has already been positioned on the bed. In this case, the bed will therefore no longer properly indicate the patient's weight. To re-measure the initial tare weight condition to obtain a proper measurement, the patient would have to be removed from the bed, which can be time consuming, cumbersome and even harmful to the patient.

Some hospital beds further include an elevation assembly which allows the bed's deck receiving the patient to be selectively raised and lowered. In some cases, medical equipment or other items may be placed under the bed's deck. Unfortunately, if the bed is lowered towards the ground surface under the deck, it may come in contact with the medical equipment or other items under the bed, which may damage the bed or the medical equipment or other items.

There is therefore a need for a system and a method which would overcome at least one of the above-identified drawbacks.

BRIEF SUMMARY

According to one aspect, there is provided a method for detecting an exit of a patient from a hospital bed, the method comprising: detecting a presence of the patient on the bed; upon detection of the patient on the bed, monitoring an indication that the patient has moved from a predetermined patient area on a patient receiving surface of the bed to outside the predetermined patient area; upon detection that the patient has moved outside the predetermined patient area, activating a bed alarm to indicate to a user that an exit of the patient from the hospital bed has been detected.

In one embodiment, detecting the presence of a patient on the bed comprises: providing a weight sensing assembly operatively connected to the bed to measure a weight of a patient received on the patient receiving surface; receiving an indication from the weight sensing assembly that the patient is received on the bed.

In one embodiment, receiving an indication from the weight sensing assembly that the patient is received on the bed comprises: the weight sensing assembly detecting a weight above a predetermined weight threshold on the bed; the weight sensing assembly providing the indication that the patient is received on the bed.

In one embodiment, the predetermined weight threshold is 32 kg.

In one embodiment, the method further comprises: after detecting the presence of the patient on the bed, detecting that the patient is in the predetermined patient area.

In one embodiment, the method further comprises: after monitoring the indication that the patient has moved from the predetermined patient area and further upon receiving a pause command, suspending monitoring the indication that the patient has moved from the predetermined patient area.

In one embodiment, suspending monitoring the indication that the patient has moved from the predetermined patient area comprises: suspending monitoring the indication that the patient has moved from the predetermined patient area for a predetermined pause time.

In one embodiment, the method further comprises: displaying a time indicative of an amount of time remaining before expiration of the predetermined pause time.

In one embodiment, the method further comprises: increasing the amount of time remaining before expiration of the predetermined pause time by a predetermined time increment.

According to another aspect, there is further provided a bed exit detection system for a hospital bed, the hospital bed including a patient receiving surface, the system comprising: a weight sensing assembly operatively connected to the bed to measure a weight of a patient received on the bed; a patient location sensor operatively connected to the patient receiving surface for determining a location of the patient on the patient receiving surface; a user interface for receiving inputs from a user; a display for providing visual indications to the user; a bed exit alarm configured for providing an indication to a user that an exit of a patient from the patient receiving surface is detected; a processing unit operatively connected to the weight sensing assembly, the patient location sensor, the user interface, the display and the bed exit alarm, the processing unit being configured to receive from the weight sensing assembly an indication that the patient is received on the bed, the processing unit being further configured to receive from the patient location sensor an indication that the patient has moved from a predetermined patient area on the patient receiving surface to outside the predetermined patient area, thereby indicating an exit of the patient from the bed, the processing unit being further configured for activating the bed exit alarm when the exit of the patient from the bed is detected.

In one embodiment, the user interface and the display include a common touchscreen.

According to yet another aspect, there is provided a method for limiting a height of a hospital bed, the hospital bed including an elevation mechanism for moving a patient receiving surface of the bed vertically relative to a ground surface, the method including: providing an indication of a minimum height value to a processing unit operatively connected to the elevation mechanism; providing a current height of the bed to the processing unit; detecting a downward vertical movement of the elevation assembly; the processing unit comparing the current height of the bed with a predetermined minimum height value; if the current height of the bed is below the predetermined minimum height value, stopping the downward movement of the elevation assembly.

In one embodiment, providing a providing a current height of the bed comprises: providing an indication of a caster height of bed casters to the processing unit; the processing unit receiving from a height sensor operatively connected to the elevation mechanism a current height of the elevation mechanism; the processing unit calculating the current height of the bed based on the indication of the caster height and the current height of the elevation mechanism.

In one embodiment, stopping the downward movement of the elevation assembly comprises: the processing unit providing a command to the elevation mechanism to stop downward movement of the elevation assembly.

In one embodiment, the method further comprises: if the current height of the bed is below the predetermined minimum height value, providing an indication to a user that the patient elevation surface is at the predetermined minimum height value.

According to still another aspect, there is also provided a method for recalibrating a tare weight condition of a hospital bed, the method comprising: providing a weight sensing assembly operatively connected to the bed; measuring a tare weight of the bed provided with medical equipment without a patient being received on the bed; storing the measured tare weight in a memory; providing the patient on the bed; upon receiving a command from a user, replacing the measured tare weight with a previously measured tare weight stored in the memory.

In one embodiment, the method further comprises: calculating a weight of the patient based on the stored tare weight.

DETAILED DESCRIPTION

Figure 1:
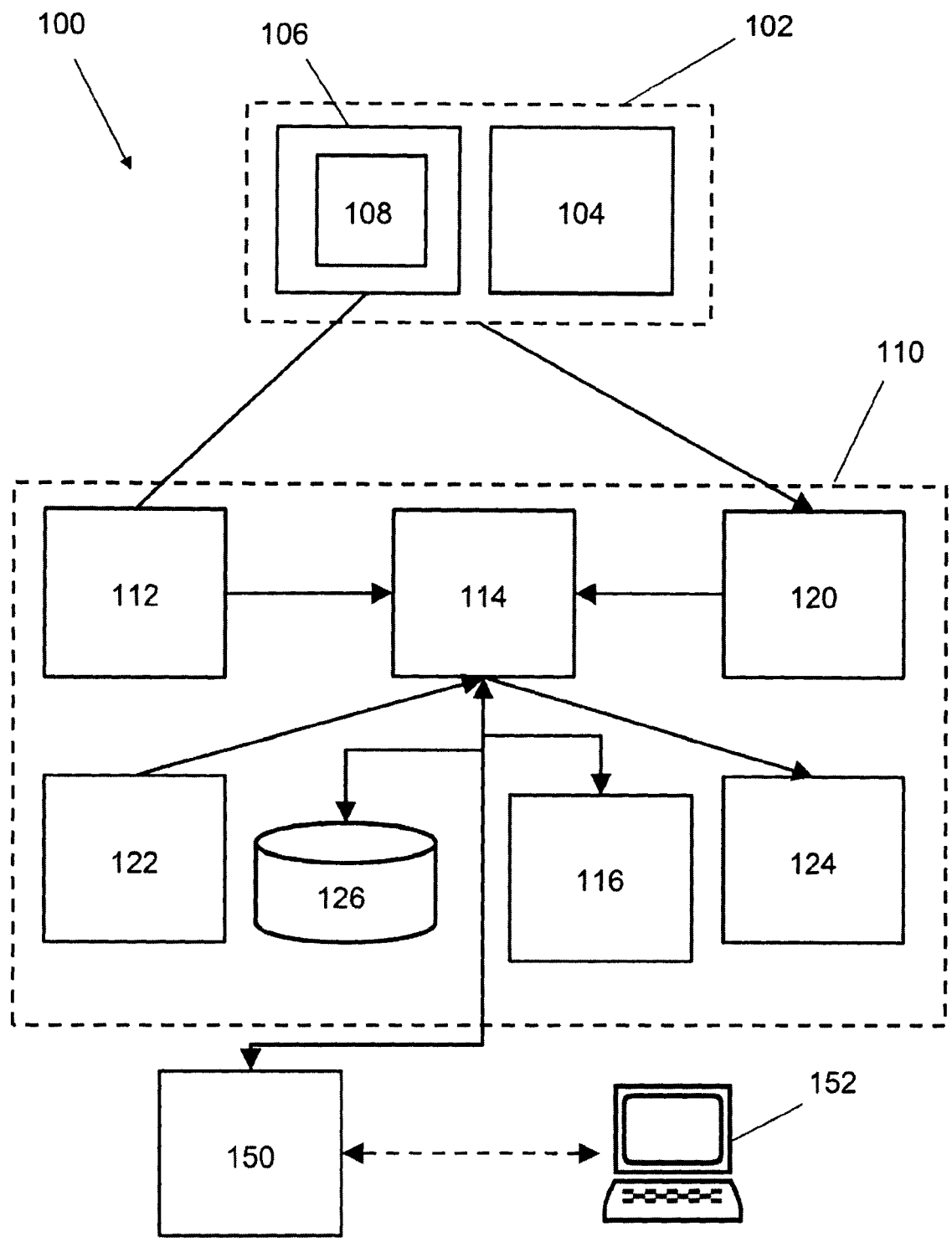
FIG. 1 is a block diagram showing a hospital bed system for a hospital bed, in accordance with one embodiment, in which the hospital bed system includes an exit detection system.

Referring first to FIG. 1, there is provided a hospital bed system 100 for a hospital bed 102, in accordance with one embodiment. It will be understood that in the following description, the term "hospital bed" is used to refer to any type of bed which is adapted to receive a patient, including hospital beds and long term care beds, and is not limited for use in a hospital.

In the illustrated embodiment, the bed 102 includes a frame 104 and a patient receiving surface 106 supported by the frame 104 for receiving a patient. Specifically, the patient receiving surface is generally rectangular and includes a deck of the hospital bed 102. The patient receiving surface 106 could further includes a mattress, not shown, disposed on the deck and onto which the patient may lie.

In the illustrated embodiment, the hospital bed system 100 further includes an exit detection system 110 for detecting an exit of a patient from the bed 102. More specifically, the exit detection system 110 includes a patient location sensor 112 operatively coupled to the bed 102 for determining a location of a patient on the bed 102, a processing unit 114 operatively coupled to the patient sensor and a bed exit alarm 116 operatively connected to the processing unit 114 for providing an indication to a user that an exit of the patient from the bed 102 has been detected. The processing unit 114 is configured for receiving from the patient location sensor 112 an indication that the patient has exited the bed 102. Specifically, the processing unit 114 may be configured for receiving from the patient location sensor 112 an indication that the patient has exited the patient receiving surface 106. Even more specifically, the processing unit 114 may be configured for receiving from the patient location sensor 106 an indication that the patient has exited a predetermined patient area 108 on the patient receiving surface 106. In this case, a detection of movement of the center of mass of the patient from the predetermined patient area 108 would be indicative of the patient exiting the bed 102, and the bed exit alarm 116 could be activated in accordance to one or more desired conditions such as a detected movement speed of the patient's center of mass on the patient receiving surface 106 and/or a period for which the patient is detected as having left the patient support surface 106.

An example of a system for determining a location of a patient on a bed, or patient location determination system, is described in U.S. Pat. No. 9,754,476, a copy of which is incorporated herein by reference. This system can be used for monitoring whether the patient is in the predetermined patient area 108 or if the patient exits the predetermined patient area 108, as a skilled person will appreciate.

In one embodiment, the predetermined patient area 108 could be rectangular and generally smaller than the patient receiving area 106, such that the predetermined patient area 108 is generally centered on the patient receiving area 106 and is surrounded by a border area of the patient receiving surface 106. Alternatively, the predetermined patient area 108 could correspond generally to the entire patient receiving surface 106.

In one embodiment, the processing unit 114 is further configured for receiving an indication that a patient is present on the bed 102 and upon receiving the indication that the patient is present on the bed 102, to set the system in a monitoring configuration in which the presence of the patient on the bed 102 is monitored. In other words, when a presence of a patient is initially detected on the bed 102, the system is "armed" and ready to detect an exit of the patient from the bed 102.

In one embodiment, the bed 102 further includes a weight sensing assembly 120 operatively connected to the patient receiving surface 104 to measure a weight of a patient received on the patient receiving surface 106. In the present embodiment, the weight sensing assembly 120 could further be used to detect the presence of a user on the bed 102. Specifically, the weight sensing assembly 120 could include one or more weight sensors disposed between the patient receiving surface 106 and the frame 104. In another embodiment, the weight sensing assembly 120 could include one or more sensors disposed between a base of the bed 102 located near the ground surface and an elevation mechanism located above the base, as described in U.S. Pat. No. 9,754,476, a copy of which is incorporated herein by reference. Alternatively, the weight sensing assembly 120 could include any other type of weight sensors or combination of weight sensors which may be located at different locations on the bed 102.

In another embodiment, instead of the weight sensing assembly 120, the processing unit 114 could be configured to detect the presence of the patient on the bed 102 using the patient location sensor 112 instead of the weight sensing assembly 120, or even using a combination of the patient location sensor 112 and of the weight sensing assembly 120.

In one embodiment, the exit detection system 110 further includes a user interface 122 operatively connected to the processing unit 114 to allow a user to input and/or modify parameters of the exit detection system 110. The bed 102 may further include a display 124 operatively connected to the processing unit 114 for displaying data related to the bed 102 to the user. In one embodiment, both the user interface 122 and the display 124 include a common touchscreen, which can both display data to a user and allow the user to input commands to the processing unit 114.

In one embodiment, the bed 102 may further include a memory 126 operatively connected to the processing unit 114 for storing one or more parameters inputted by the user via the user interface 122.

In one embodiment, the bed exit alarm 116 includes a visual indicator operatively connected to the processing unit 114. Specifically, the visual indicator may include one or more indicator lights, such as LED-based lights or incandescent lights, which may be located on an exterior surface of the bed 102 such as a side surface of the bed 102 so as to be visible to a user standing away from the bed. The indicator lights may provide to the user a visual indication of a specific condition or event, such as an exit of the patient from the bed 102. For example, the processing unit 114 may be configured to cause the indicator lights to flash intermittently when an exit of the patient from the bed 102 is detected.

Moreover, the indicator lights may each be configured to be selectively lit in one of a plurality of colors depending on the visual indication which is to be provided to the user. For example, the processing unit 114 may be configured to cause the indicator lights to be lit up in an orange color and to flash intermittently to provide an indication that an exit of the patient from the bed 102 is detected. The processing unit 114 may further be configured to cause the indicator lights to be lit up in a green color and to remain continuously lit when the system 110 is armed, but that no exit of the patient from the bed 102 is detected. It will be understood that other colors and other combinations are also possible.

The bed exit alarm 116 may further include an audible alarm which produces a sound indicative of the patient exiting the bed 102. The bed exit alarm 116 could also be remote from the bed 102, at a control station operatively connected to multiple hospital beds for example.

Figure 2:
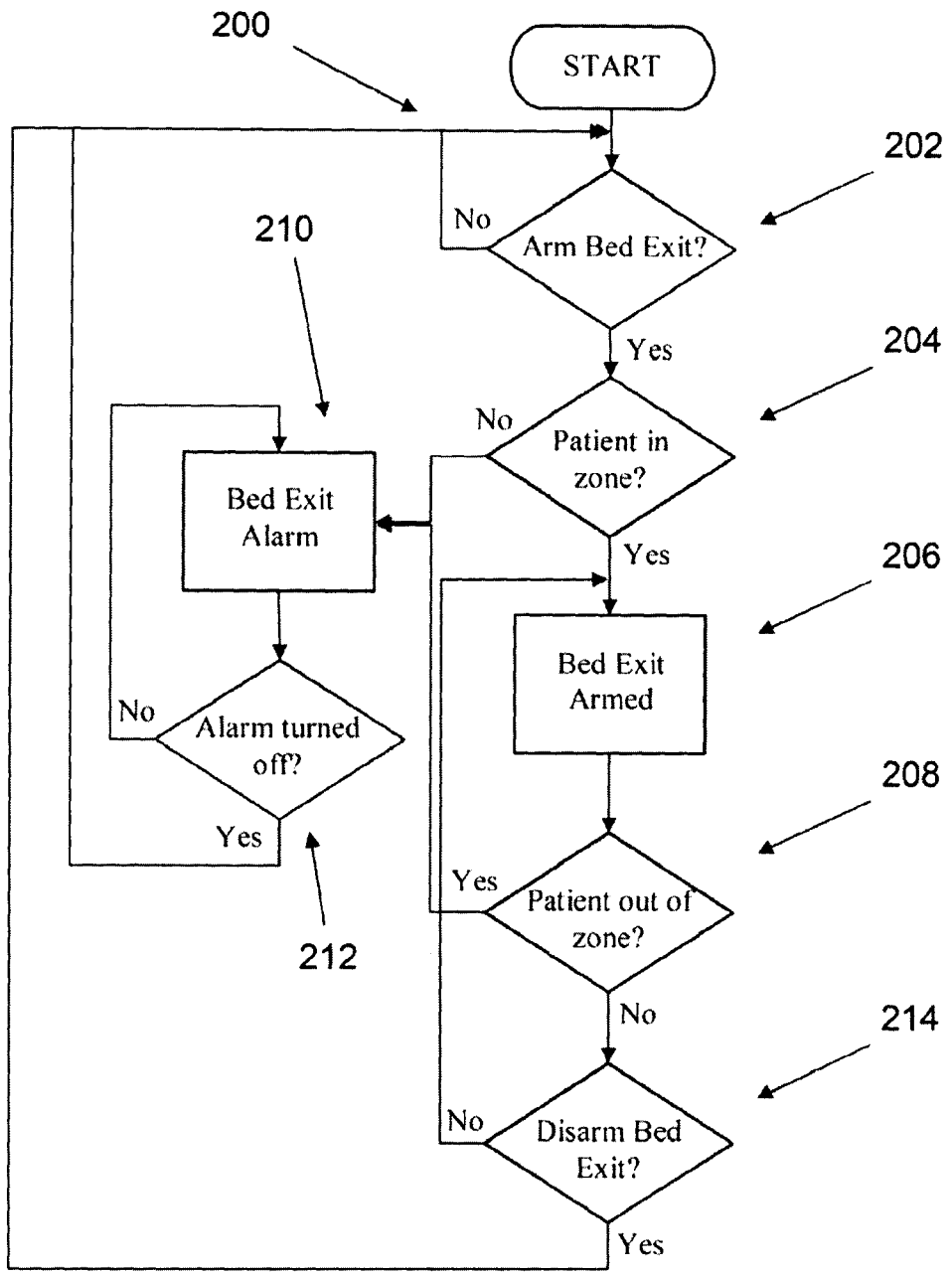
FIG. 2 is a flowchart of a manual activation mode of a method for detecting an exit of a patient from the bed, in accordance with one embodiment.
Figure 3:
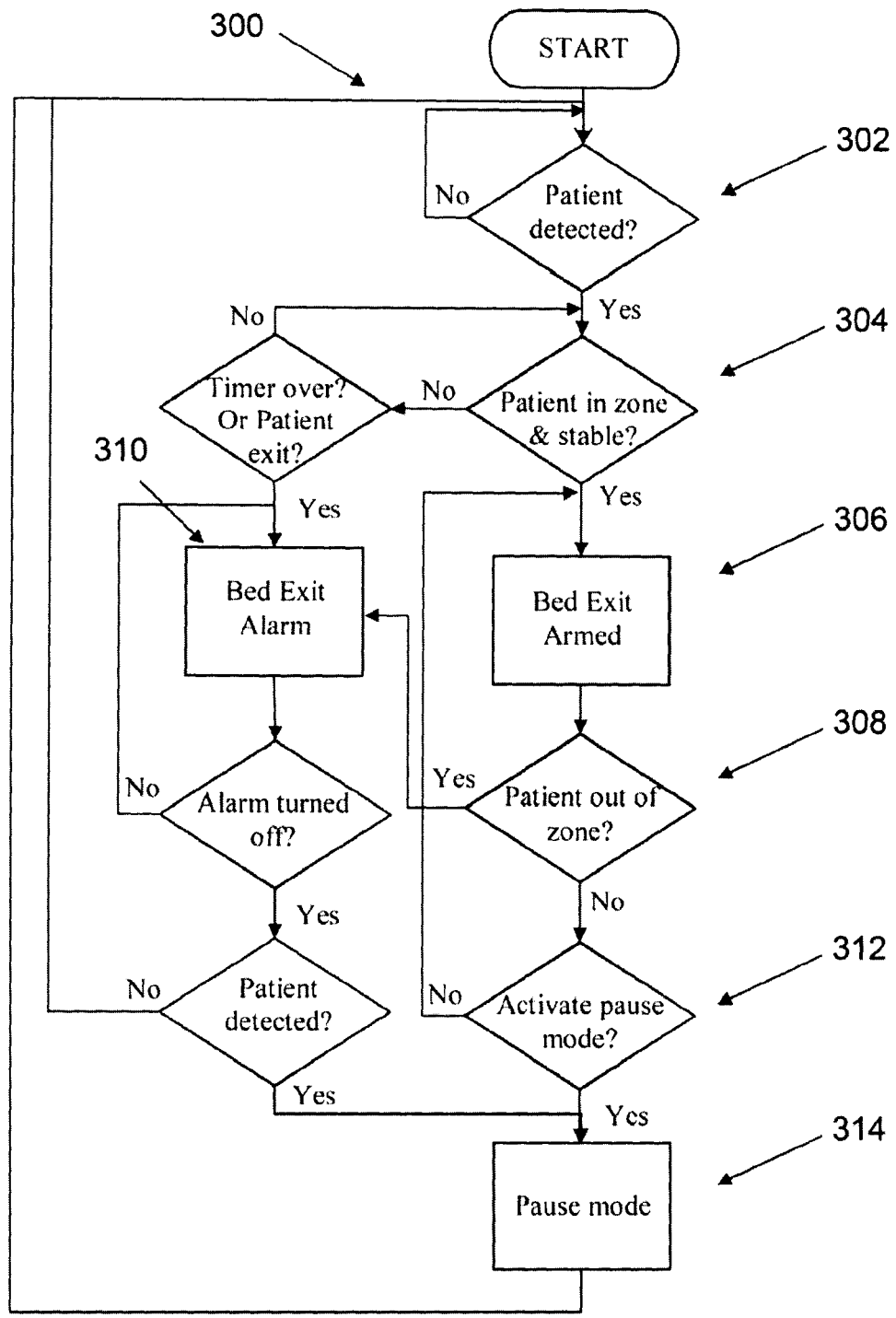
FIG. 3 is a flowchart of an automatic activation mode of a method for detecting an exit of a patient from the bed, in accordance with one embodiment.

Now turning to FIGS. 2 and 3, there is shown a method for detecting an exit of a patient from the bed 102, in accordance with one embodiment.

In this embodiment, the system 110 is first set into one of a manual activation mode 200, illustrated in FIG. 2, and an automatic activation mode 300, illustrated in FIG. 3.

Referring first to FIG. 2, in the manual activation mode 200, the system 110 is first simply armed by a user, in accordance with 202. Specifically, the user may manually input into the user interface 122 a command to start monitoring an exit of the patient from the bed 102. The processing unit 114, operatively coupled to the user interface 122, receives the command to start monitoring the exit of the patient. According to 204, the system 110 first confirms that the patient is in the predetermined patient area 108 on the bed 102.

In one embodiment, before the user manually inputting the command to start monitoring the exit of the patient from the bed 102, the patient is placed on the bed 102 and the user visually confirms that the patient is properly received on the patient receiving surface 106. In one embodiment, the user must specifically confirm that the patient is in the predetermined patient area 108 of the patient receiving surface 106, such that the exit of the patient from the predetermined patient area 108 may then be monitored.

According to 206, the bed exit detection system 110 is then armed such that the exit of the patient from the predetermined patient area 108 is monitored. While monitoring the exit of the patient from the bed 102, the processing unit 114 may further cause the indicator lights to provide to a user an indication that the exit of the patient from the bed 102 is being monitored. For example, the indicator lights may be lighted continuously in a green color. Alternatively, the indicator lights may flash in a predetermined pattern and/or be lighted in a different color. In yet another embodiment, the system 110 may only provide an indication to the user that the exit of the patient from the bed 102 is being monitored via the display 124, rather than via the indicator lights.

According to 208, when the patient location sensor 112 detects that the patient location moves from the predetermined patient area or zone 108 to outside the predetermined patient area 108, the processing unit 114 receives an indication that the patient is exiting the bed 102 and activates the bed exit alarm 116 in accordance with 210. Specifically, the processing unit 114 lights the indicator lights in an orange color and causes the indicator lights to flash intermittently, thereby providing to a user standing near the bed an indication that the patient is exiting the bed 102.

According to 212, the user may then manually deactivate the bed exit alarm 116. For example, the bed exit alarm 116 may be deactivated by the user via the touchscreen. Alternatively, the bed exit alarm 116 could also be deactivated automatically after a predetermined bed alarm time.

Furthermore, according to 214, even if the bed exit alarm 116 has not been activated, the user may still interrupt the monitoring of the exit of the patient from the bed 102 manually, by entering a corresponding input command into the user interface 122, for example.

Referring now to FIG. 3, instead of being set in the manual activation mode 200, the system 110 may be set in the automatic activation mode 300.

If a command to set the system in the automatic activation mode 300 is received, the presence of a patient on the bed 102 is first monitored in accordance with 302. Specifically, the presence of a patient on the patient receiving surface 106 is monitored. In one embodiment, the presence of a patient on the patient receiving surface 106 is monitored using the weight sensing assembly 120. For example, the weight sensing assembly 120 may provide to the processing unit 114 an indication that a patient is received on the bed 102 when a weight above a predetermined weight threshold has been detected on the bed 102. In one embodiment, the predetermined weight threshold is 70 lb or about 32 kg. It will be appreciated that this weight threshold may contribute to confirming that a patient is actually received on the bed, rather than merely one or more objects being deposited on the bed or someone leaning on the bed. Alternatively, the predetermined weight threshold could be more or less than 70 lb or about 32 kg.

In one embodiment, before the indication that the patient is received on the bed 102 is received by the processing unit 114, the patient location sensor 112 may be in a non-active mode in which the location of the patient on the patient receiving surface 106 is not monitored. Specifically, the patient location sensor 112 can simply be turned off, such that it does not require any power and therefore does not consume any energy. Alternatively, the patient location sensor 112 could be in a low-power mode which requires relatively little power and therefore consumes relatively little energy.

In one embodiment, once the indication that the patient is on the bed 102 is provided by the weight sensing assembly 120 and received by the processing unit 114, the indication is provided by the processing unit 114 to the display 124 and is displayed on the display 124.

According to 304, the processing unit is configured to receive an indication that the patient is positioned in the predetermined patient area 108 and that the patient is not moving, or stable.

Figure 4:
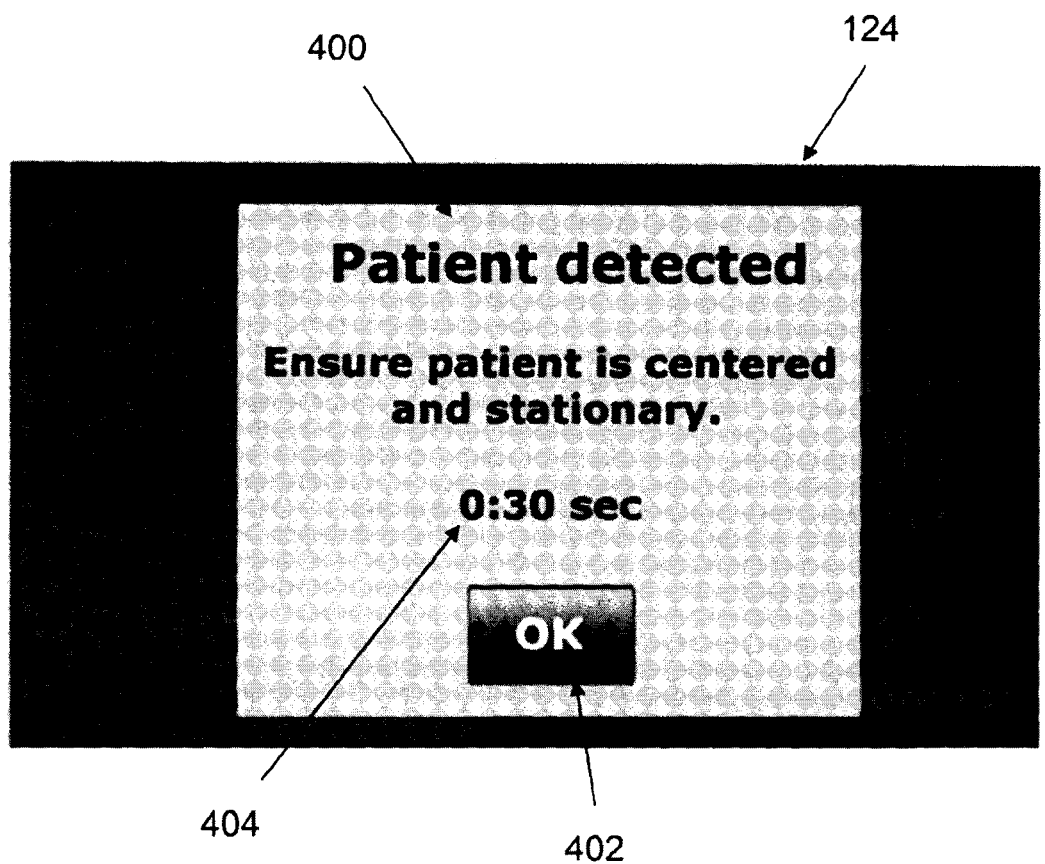
FIG. 4 is a diagram of a touchscreen for the hospital bed system illustrated in FIG. 1, displaying a window including text indicating that the presence of a patient has been detected on the bed.

Referring now to FIG. 4, the indication may include a window 400 including text indicating that the presence of the patient has been detected on the bed 102 and a confirmation button 402 which can be activated by the user to provide the indication that the patient is positioned in the predetermined patient area 108 and that the patient is stable.

In an embodiment in which the display 124 and the user interface 122 is a touchscreen, the user may activate the confirmation button 402 by interacting with the touchscreen.

Alternatively, instead of the user providing the indication that the patient is in the predetermined patient area 108 and stable, the indication may be provided automatically by the patient location sensor 112. For example, the indication may be provided if the presence of the patient in the predetermined patient area 108 is detected and if no movement of the patient on the patient receiving surface 106 is detected for a predetermined time. On the other hand, if movement of the patient is detected, or if the presence of the patient on the bed 102 is detected but the presence of the patient in the predetermined patient area 108 is not detected, indicating that the patient is on the bed 102 but not properly placed in the predetermined patient area 108, then the patient location sensor 112 will not provide the indication that the patient is in the predetermined patient area 108 and stable.

In one embodiment, the window 400 may further include a decreasing timer 404 indicating an amount of time remaining before expiration of a first predetermined time. If the indication that the patient is in the predetermined patient area 108 and stable is not provided before expiration of the first predetermined time, the bed exit alarm 116 is activated by the processing unit 114. In one embodiment, the first predetermined time is 60 seconds. Alternatively, the first predetermined time may be longer or shorter.

In one embodiment, the bed exit alarm 116 includes the processing unit 114 lighting the indicator lights in an orange color and causes the indicator lights to flash intermittently, as described above. Alternatively, the bed exit alarm 116 could include other types of alarms.

Referring back to FIG. 3, once the indication that the patient is in the predetermined patient area 108 and stable is received by the processing unit 114, the exit of the patient from the predetermined patient area 108 may then be monitored using the patient location sensor 112 in accordance with 306. While monitoring the exit of the patient from the bed 102, the processing unit 114 may cause the indicator lights to provide to a user an indication that the exit of the patient from the bed 102 is being monitored, for example by lighting the indicator lights continuously in a green color as described above.

According to 308, when the patient location sensor 112 detects that the patient location moves from the predetermined patient area or zone 108 to outside the predetermined patient area 108, the processing unit 114 receives an indication that the patient is exiting the bed 102 and activates the bed exit alarm 116 in accordance with 310 and as described above. Specifically, the processing unit 114 lights the indicator lights in an orange color and causes the indicator lights to flash intermittently, thereby providing to a user standing near the bed an indication that the patient is exiting the bed 102.

According to 312, during the monitoring of the exit of the patient from the bed 102, the user may input a pause command which sets the system in a pause mode 314 in which the monitoring of the exit of the patient from the bed 102 is temporarily interrupted. Specifically, even if the patient moves or is moved from the predetermined patient area 108 to outside the predetermined patient area 108 while the system is set in the pause mode 314, the bed exit alarm 116 will not be activated.

It will be appreciated that it may be desirable to temporarily interrupt the monitoring of bed exit to access the patient in order to provide care to the patient, which may require temporarily moving the patient outside of the predetermined patient area 108. Care to the patient could include washing the patient, performing examinations on the patient, changing the sheets, or any other type of care.

In one embodiment, when the pause command is received, a pause indicator is also activated, thereby indicating to the user that the bed exit system is in the pause mode 314. In one embodiment, the pause indicator includes the indicator light being lighted continuously in an orange color. Alternatively, the pause indicator may include another visual indicator or any other type of indicator.

Figure 5:
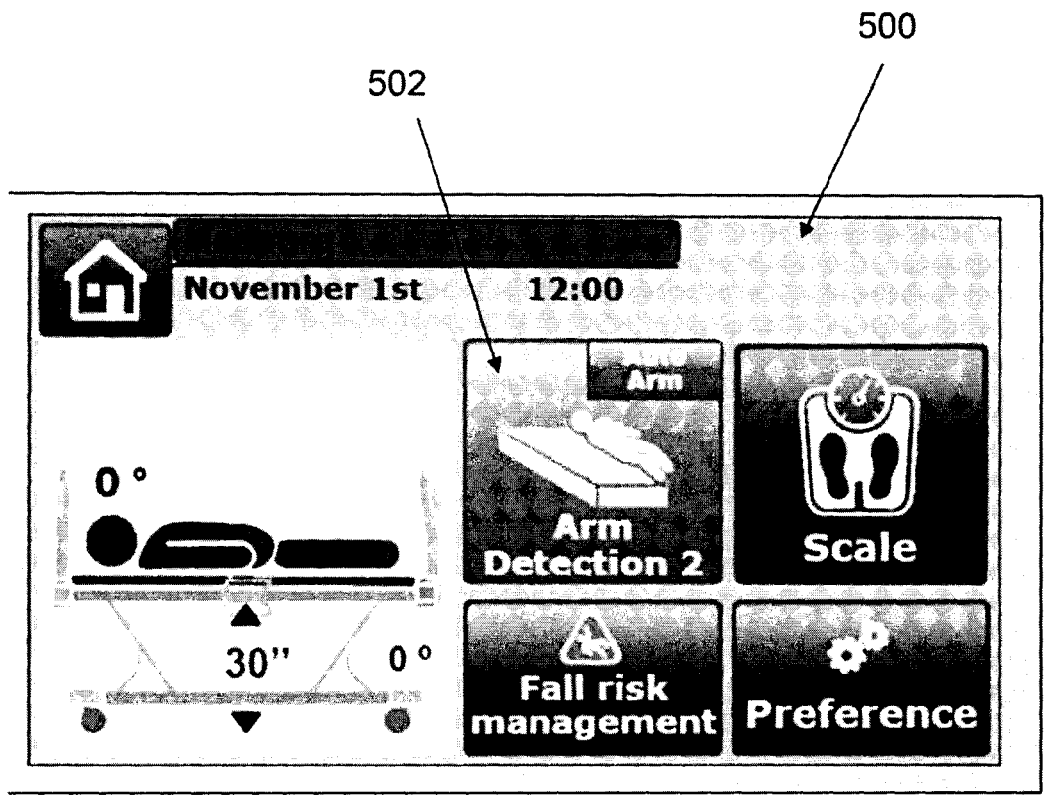
FIG. 5 is another diagram of the touchscreen for the hospital bed system illustrated in FIG. 1, displaying a main interface image during monitoring of the exit of the patient from the bed.

FIG. 5 shows a main interface image 500 which may be displayed on the display 124 during monitoring of the exit of the patient from the bed 102. The main interface image 500 could include an indication that the system 110 is armed and that the exit of the patient from the bed 102 is therefore monitored.

Figure 6:
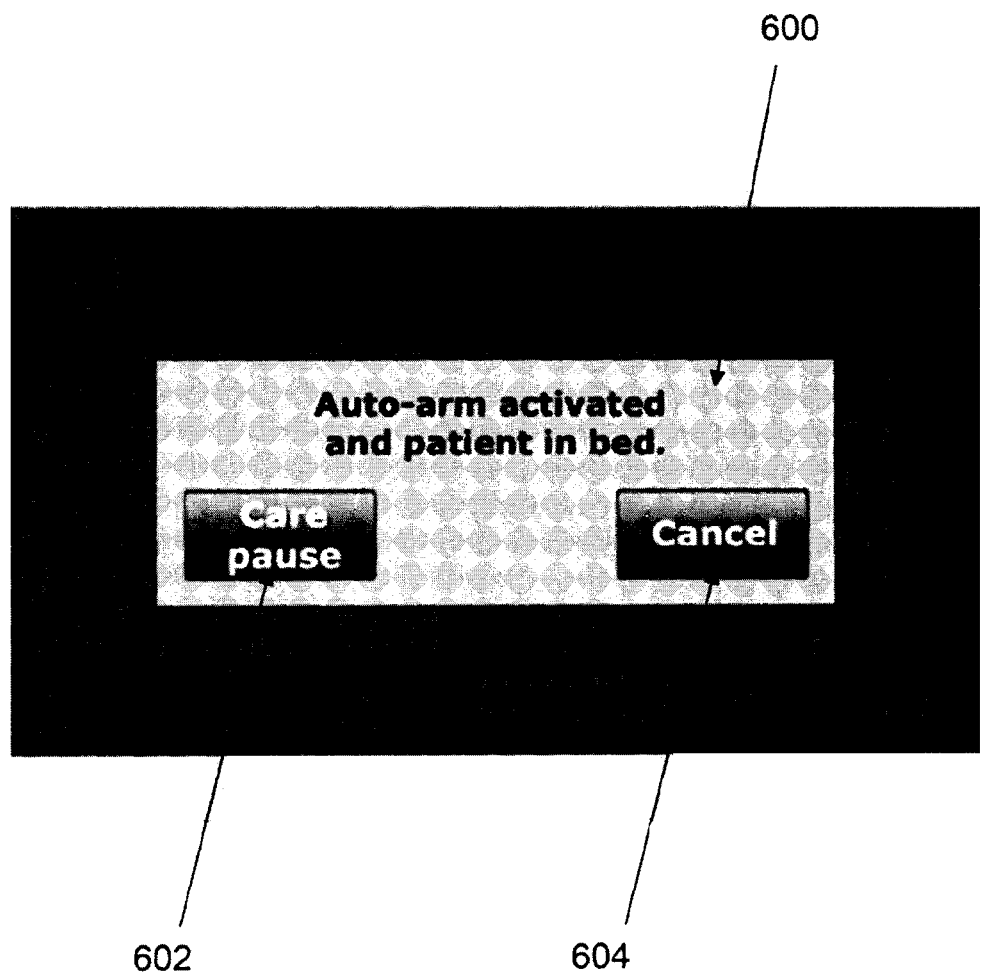
FIG. 6 is yet another diagram of the touchscreen for the hospital bed system illustrated in FIG. 1, displaying a pause confirmation window which allows a user to input a pause command.

In the illustrated embodiment, the main interface image 500 includes a pause button 502 which can be activated by the user to display a pause confirmation window 600, as shown in FIG. 6. In the illustrated embodiment, the pause confirmation window 600 includes a confirmation button 602 which can be activated by the user to provide a pause command to the processing unit 114. Still in the illustrated embodiment, the pause confirmation window 600 further includes a cancellation button 604 which closes the pause confirmation window 600 and returns the display 124 to the main interface image 500 shown in FIG. 5.

Figure 7:
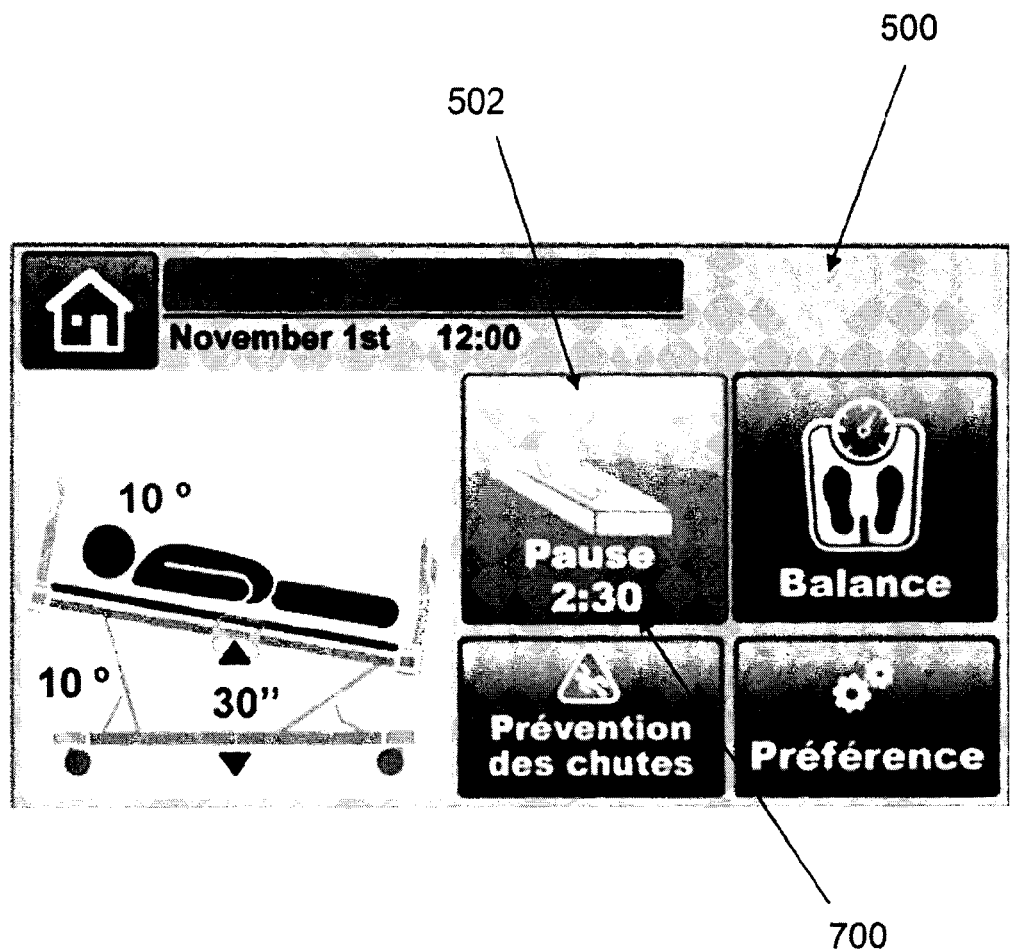
FIG. 7 is still another diagram of the touchscreen for the hospital bed system illustrated in FIG. 1, displaying again the main interface image while the exit detection system is in a pause mode and including a decreasing timer indicating an amount of time remaining before expiration of a predetermined pause time.

Once the confirmation button has been activated by the user, the main interface image 500 may be displayed on the display 124 and may include text indicative that the system 110 is currently set in the pause mode 314. In the illustrated embodiment, the main interface image 500 further includes a decreasing timer 700 indicating an amount of time remaining before expiration of a predetermined pause time. Specifically, the decreasing timer 700 may be displayed on the pause button 502, as shown in FIG. 7.

Figure 8:
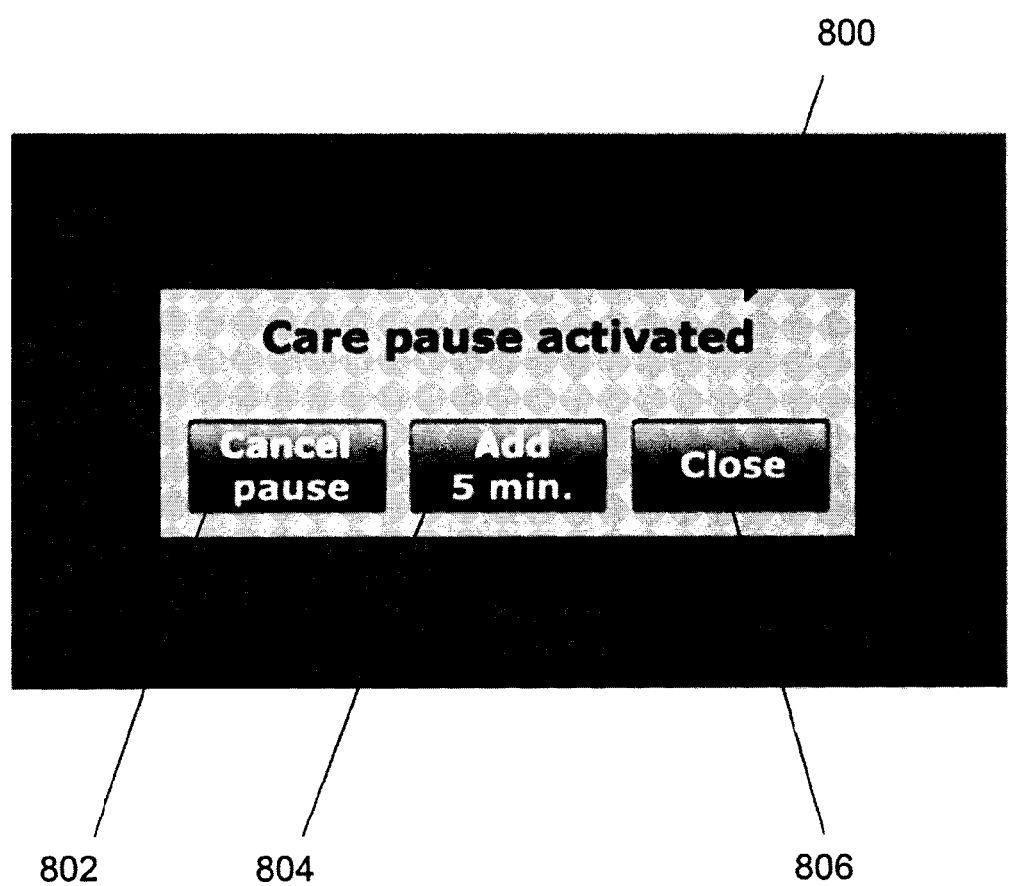
FIG. 8 is another diagram of the touchscreen for the hospital bed system illustrated in FIG. 1, displaying a pause option window which allow the user to selectively exit the pause mode and to increase the amount of time remaining before expiration of the predetermined pause time.

When the system 110 is in the pause mode 314, the pause button 502 may further be activated by the user to display a pause option window 800, as shown in FIG. 8. In the illustrated embodiment, the pause option window 800 includes a pause cancellation button 802, a timer increase button 804 and a window closing button 806. The pause cancellation button 802 can be activated by the user to exit the pause mode 314 and the method can be repeated from step 302, starting again with monitoring the presence of the patient on the bed 102. The timer increase button 804 can be activated by the user to increase the amount of time remaining before expiration of the predetermined pause time by a predetermined time increment. In one embodiment, the predetermined pause time is initially 2.5 minutes and the predetermined time increment is 5 minutes. Alternatively, the initial predetermined pause time and the predetermined time increment may be different. Finally, the window closing button 806 can be activated by the user to close the pause option window 800 and return the display to the main interface image 700 shown in FIG. 7.

After expiration of the predetermined pause time, the system 110 exits the pause mode 314. Specifically, the presence of the patient on the bed 102 is once again monitored, and the system may repeat step 302 and the following steps.

In one embodiment, in addition to the system 110 being set in the pause mode 314 upon receipt of a pause command from the user, the system 110 may further be set to pause mode 314 when the processing unit 114 receive an indication that, following a manual deactivation of the bed exit alarm 116 by the user, a patient is still received on the bed in accordance with 316 of FIG. 3. This could indicate that the user wants to temporarily suspend the monitoring of bed exit while attending to the patient on the bed 102.

It will be appreciated that the use of the automatic activation mode 300 advantageously allows the patient location sensor 112 to only be activated and used if the presence of a patient on the bed 102 is first detected, which reduces the overall energy consumption of the system 110.

Furthermore, by providing a visual indication to the user that a patient is received on the bed 102 by displaying window 400, the system 110 further provides to the user an indication that the patient must be placed properly in the predetermined patient area 108, thereby contributing to ensure that the user confirms that the user is in the predetermined patient area 108 before the start of the monitoring of the patient exiting the bed 102. This may help to prevent situation in which the patient is outside the predetermined patient area 108 when the monitoring of the patient exiting the bed 102 is started, in which case the bed exit alarm 116 would immediately be activated.

The use of the pause mode 314 may also contribute to preventing the user from forgetting to re-arm the bed exit detection system 110 once the system 110 is interrupted in order to provide care to the patient.

In one embodiment, the processing unit 114 may further be configured to allow a tare weight condition to be measured to obtain proper measurements from the weight sensing assembly 120 and from the patient location sensor 112. Specifically, measuring the tare weight condition includes installing required medical equipment on the bed 102, the processing unit 114 receiving a measure of weight and of patient location from the weight sensing assembly 120 and from the patient location sensor 112 before the patient is received on the bed 102 and storing the initial weight measurement the initial location measurement in the memory 126. This initial weight measurement will therefore represent a value of zero, with further weight measured by the weight sensing assembly 120 representing a difference between the measured weight and the initial weight measurement. Similarly, the initial patient location measurement will represent a value of zero, or a location centered on the patient receiving surface, with further location measurement by the patient location system being calculated according to this initial position measurement.

Figure 9:
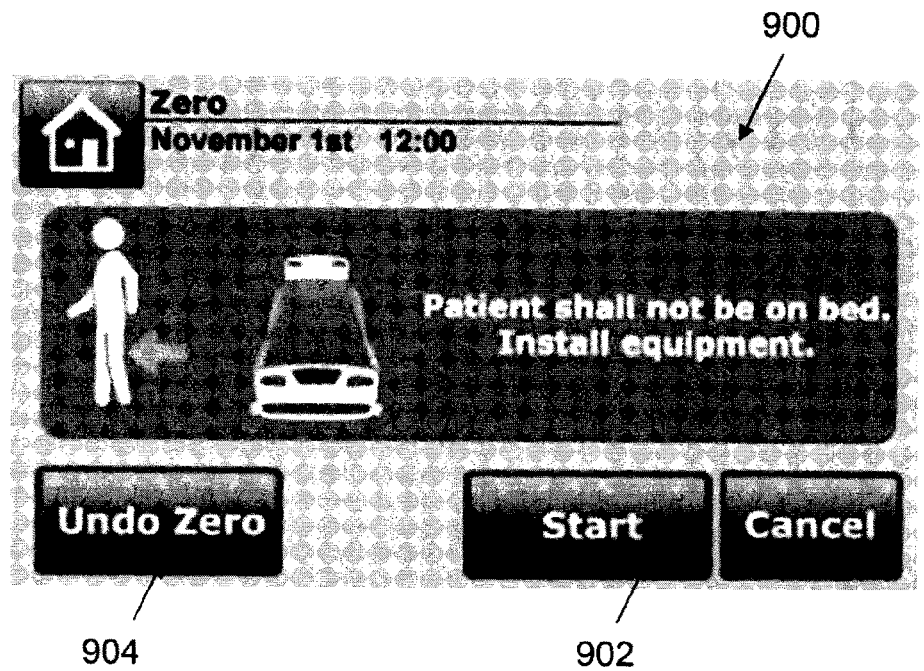
FIG. 9 is a diagram of the touchscreen for the hospital bed system illustrated in FIG. 1, displaying a calibration menu image including a start button and a tare weight condition recall button.

FIG. 9 shows a calibration menu image 900 displayed on the display 124. In this embodiment, the calibration menu image 900 includes a start button 902 which can be activated by the user to instruct the processing unit 114 to receive the initial weight and location measurements.

Figure 10:
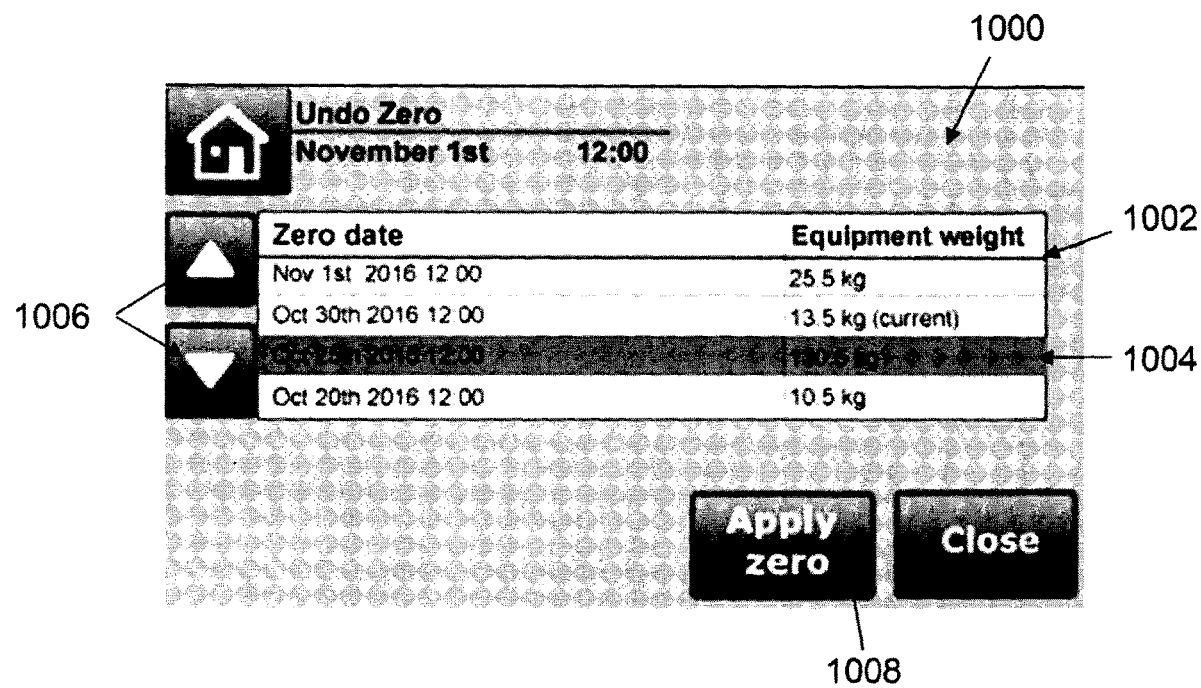
FIG. 10 is another diagram of the touchscreen for the hospital bed system illustrated in FIG. 1, displaying a tare weight condition recall menu image including text indicative of a plurality of previous measured tare weight conditions.

In the illustrated embodiment, the calibration menu image 900 further includes a tare weight condition recall button 904 which can be activated by the user to cause the display to display a tare weight condition recall menu image 1000 as shown in FIG. 10. The tare weight condition recall menu image 1000 includes text indicative of a plurality of previous measured tare weight conditions 1002, a cursor 1004 for selecting one of the previous measured tare weight conditions 1002 and a pair of scroll buttons 1006 to move the cursor 1004 between the previous measured tare weight conditions 1002. In the illustrated embodiment, the plurality of previous measured tare weight conditions 1002 includes the last four tare weight conditions measured. Alternatively, the plurality of previous measured tare weight conditions 1002 could include more or less previously measured tare weight conditions. Still in the illustrated embodiment, the tare weight condition recall menu image 1000 includes an apply button 1008 which can be activated by the user to apply the selected tare weight condition such that the current tare weight condition are replaced by the selected tare weight condition.

Figure 11:
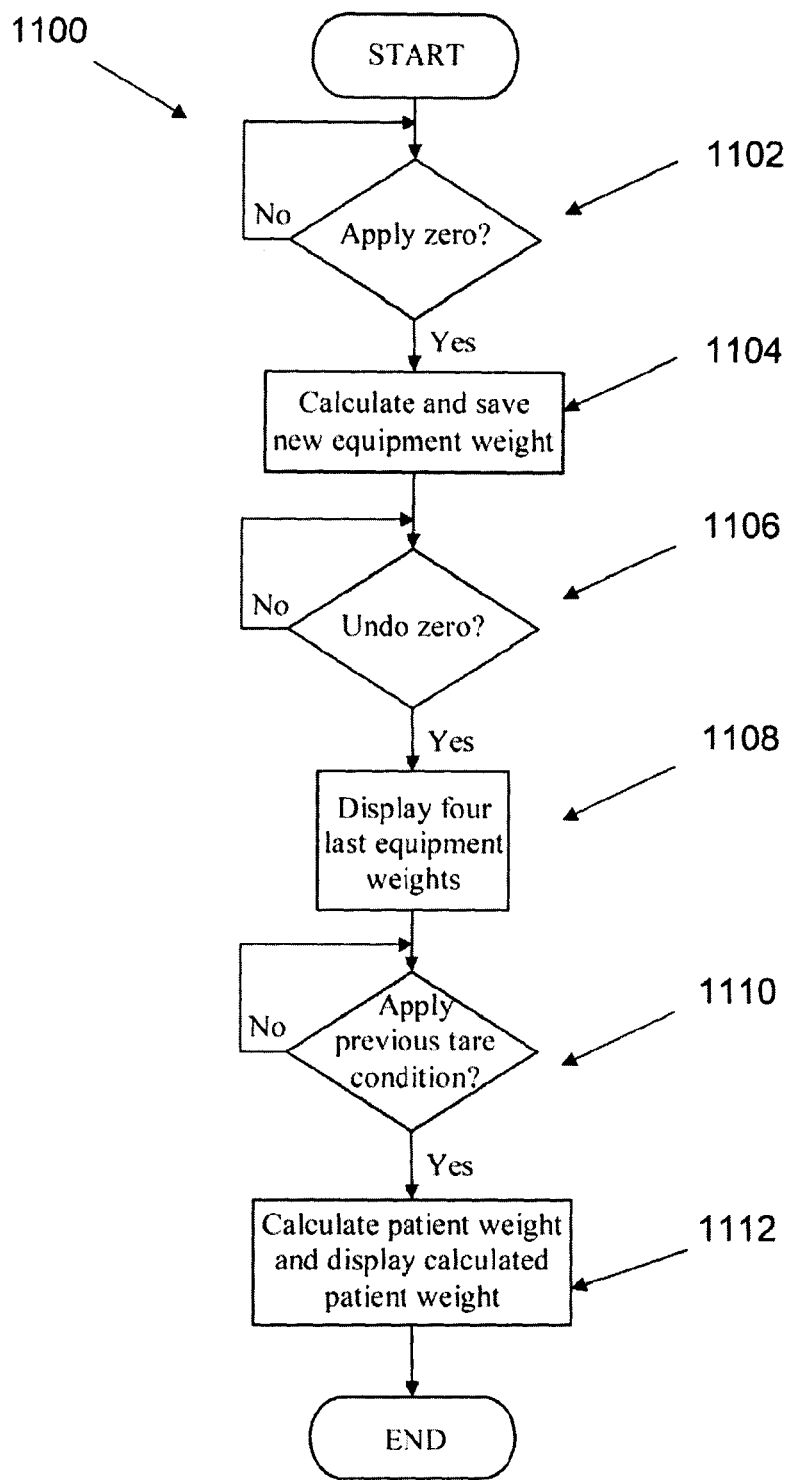
FIG. 11 is a flowchart of a method for recalibrating a tare weight condition of a hospital bed, in accordance with one embodiment.

Now referring to FIG. 11, there is provided a method 1100 for recalibrating a tare weight condition of a hospital bed, in accordance with one embodiment.

According to 1102, the user first inputs a command for applying the current measured tare weight condition, also referred to as "zero", to the processing unit 114 via the user interface 122.

According to 1104, the processing unit receives from the weight sensing assembly 120 an indication of the bed weight and of the current measured weight. In this embodiment, medical equipment is received on the bed 102 and creates a difference between the bed weight and the current measured weight. Therefore, the processing unit 114 calculates the difference between the bed weight and the current measured weight representing the equipment weight. The equipment weight may further be stored in the memory 126, where it is associated to a tare weight condition which includes a current weight measurement and a current location measurement.

According to 1106, when the user inputs a command to recall the previous tare weight conditions, the processing unit 114 receives the command. The processing unit 114 therefore communicates with the memory 126 to retrieve the predetermined number of tare weight conditions stored in the memory 126.

According to 1108, the last four tare weight conditions are then displayed on the display 124, as described above. Specifically, each tare weight condition is associated with an equipment weight, which was calculated as explained above.

According to 1110, the user selects the tare weight condition based on the appropriate equipment weight corresponding to the equipment weight currently on the bed 102 and the selected tare weight condition is applied. Specifically, according to 1112, the patient weight can be calculated as the difference between the current measured weight and a sum of the bed weight and the selected equipment weight, and the calculated weight may be displayed on the display 124.

It will be appreciated that this method advantageously acts as an "undo" function in case the tare weight condition is mistakenly measured and set while the patient is received on the bed. With the present method, the tare weight conditions can be set to an accurate value based on a previous measurement without having to remove the patient from the bed 102 to perform a tare weight condition measurement again.

In one embodiment, the processing unit 114 is further adapted to display an image including a plurality of command buttons which can be activated by the user and which may each be provided with a pictogram which is related to the function of the command button. This may help facilitate the use of the user interface. Pictograms may also be used to show different data or indication related to the bed or to the safety of the patient received on the bed.

In one embodiment, the bed system 100 further includes a communication unit 150 operatively connected to the processing unit 114, as shown in FIG. 1, for allowing communication of the processing unit 114 with a remote device 152. In one embodiment, the remote device 152 is a personal computer. Alternatively, the remote device 152 could be a smartphone, a tablet of any other types of devices.

In one embodiment, the communication unit 150 includes a WiFi antenna adapted for wirelessly communicating with the remote device. Alternatively, the communication unit 150 could include a USB port for connecting the remote device 152 to the processing unit using a USB cable and protocol.

In one embodiment, the remote device 152 includes a computer program which enables the exchange of data between the remote device 152 and the processing unit 114 and the memory 126. In one embodiment, the computer program is accessible through a web browser.

In one embodiment, the computer program is configured to receive one or more images or pictograms provided by the user and to format the one or more images or pictograms so as to make them compatible with the processing unit 114 of the bed 102. The computer program may further be configured to allow access to the processing unit 114 for troubleshooting purposes.

It will be appreciated that the computer program may be used to transfer data to and from processing units of multiple beds simultaneously.

Figure 12:
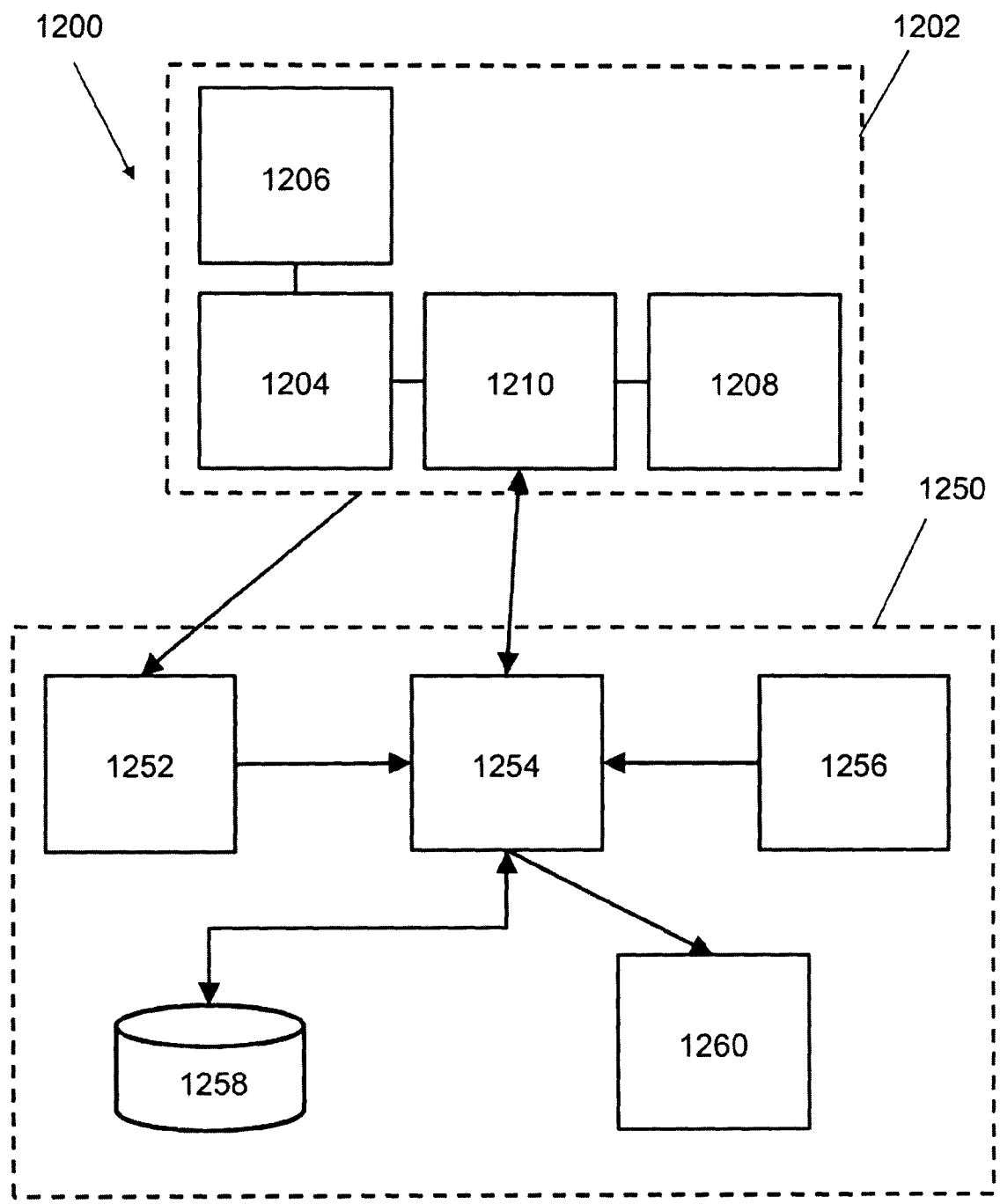
FIG. 12 is a block diagram showing a hospital bed system for a hospital bed, in accordance with an alternative embodiment, in which the hospital bed includes an elevation mechanism and a bed height limiting system.

Now turning to FIG. 12, there is shown a hospital bed system 1200 for a hospital bed 1202, in accordance with another embodiment.

In this embodiment, the bed 1202 includes a frame 1204 and a patient receiving surface 1206 supported by the frame 1204 for receiving a patient. Specifically, the patient receiving surface is generally rectangular and includes a deck of the hospital bed 1202. The patient receiving surface 1206 could further includes a mattress, not shown, disposed on the deck and onto which the patient may lie.

Still in the embodiment illustrated in FIG. 1200, the bed 1202 further includes an elevation mechanism 1210 secured to the frame 1204 and located under the frame 1204 for moving the patient receiving surface 1206 vertically relative to a ground surface on which the bed 1202 is placed.

In one embodiment, the elevation mechanism 1210 may include a front elevation assembly located near a front end of the bed 1202 and a rear elevation assembly located near a rear end of the bed 1202. This configuration allows the bed 1202 to be angled relative to the ground surface by actuating one of the front and rear lift assemblies such that one of the front and rear ends of the bed 1202 is located higher than the other one of the front and rear ends of the bed 1202. To raise or lower the bed, both the front elevation assembly and the rear elevation assembly are actuated simultaneously such that the front and rear ends of the bed are raised or lowered simultaneously. Each one of the front and rear elevation assembly may include one or more actuators such as linear actuators or any other type of actuators which is skilled person would consider to be appropriate.

An example of an elevation mechanism, or elevation system, is described in US Patent Publication No. 2016/0058639, a copy of which is incorporated herein by reference. Alternatively, the elevation mechanism could be configured differently.

In the illustrated embodiment, the bed 1202 further includes a plurality of casters 1208, and the front and rear elevation assemblies extend between the casters 1208 and the patient receiving surface. Alternatively, the bed 1202 may not include casters.

Still in the illustrated embodiment, the hospital bed system 1200 further includes a bed height limiting system 1250 for limiting the height of the patient support surface 1206 to a minimum height. The bed height limiting system 1250 includes a height sensor 1252 operatively connected to the bed 1202, a processing unit 1254 operatively connected to the bed 1202 and a user interface 1256 operatively connected to the processing unit 1254. The processing unit 1254 is configured for receiving a minimum height value provided by the user via the user interface 1256. In one embodiment, the bed height limiting system 1250 further includes a memory 1258 operatively connected to the processing unit 1254 for storing the minimum height value.

In one embodiment, the height sensor 1252 is operatively connected to the actuators of the elevation mechanism 1210. Specifically, the processing unit 1254 may be configured to calculate a height between a bottom end and a top end of the front and rear elevation assemblies by receiving a measurement of extension from the actuators, corresponding to a length by which the actuators are extended. Alternatively, the height sensor may instead include another type of sensor such as an optical sensor or any other type of sensor which a skilled person would consider appropriate.

In one embodiment, the processing unit is configured to calculate the height of the patient support surface 1206 relative to the ground surface by adding the calculated height of the elevation mechanism 1210 with a height of the casters 1208. In one embodiment, the height of the casters 1208 is pre-entered in the memory 1258 and is provided to the processing unit 1254 from the memory 1258. Alternatively, the user may enter the height of the casters 1208 manually in the memory 1258 through the user interface 1256.

In the illustrated embodiment, the processing unit 1254 is further operatively connected to the elevation mechanism 1210 and is configured to detect a downward motion of the elevation mechanism.

In one embodiment, the bed 1202 may further include a display 1260 operatively connected to the processing unit 1254 for displaying data related to the bed 1202 to the user. In one embodiment, both the user interface 1256 and the display 1260 include a touchscreen, which can both display data to a user and allow the user to input commands to the processing unit 1254 and to provide parameters into the memory 1258.

Figure 13:
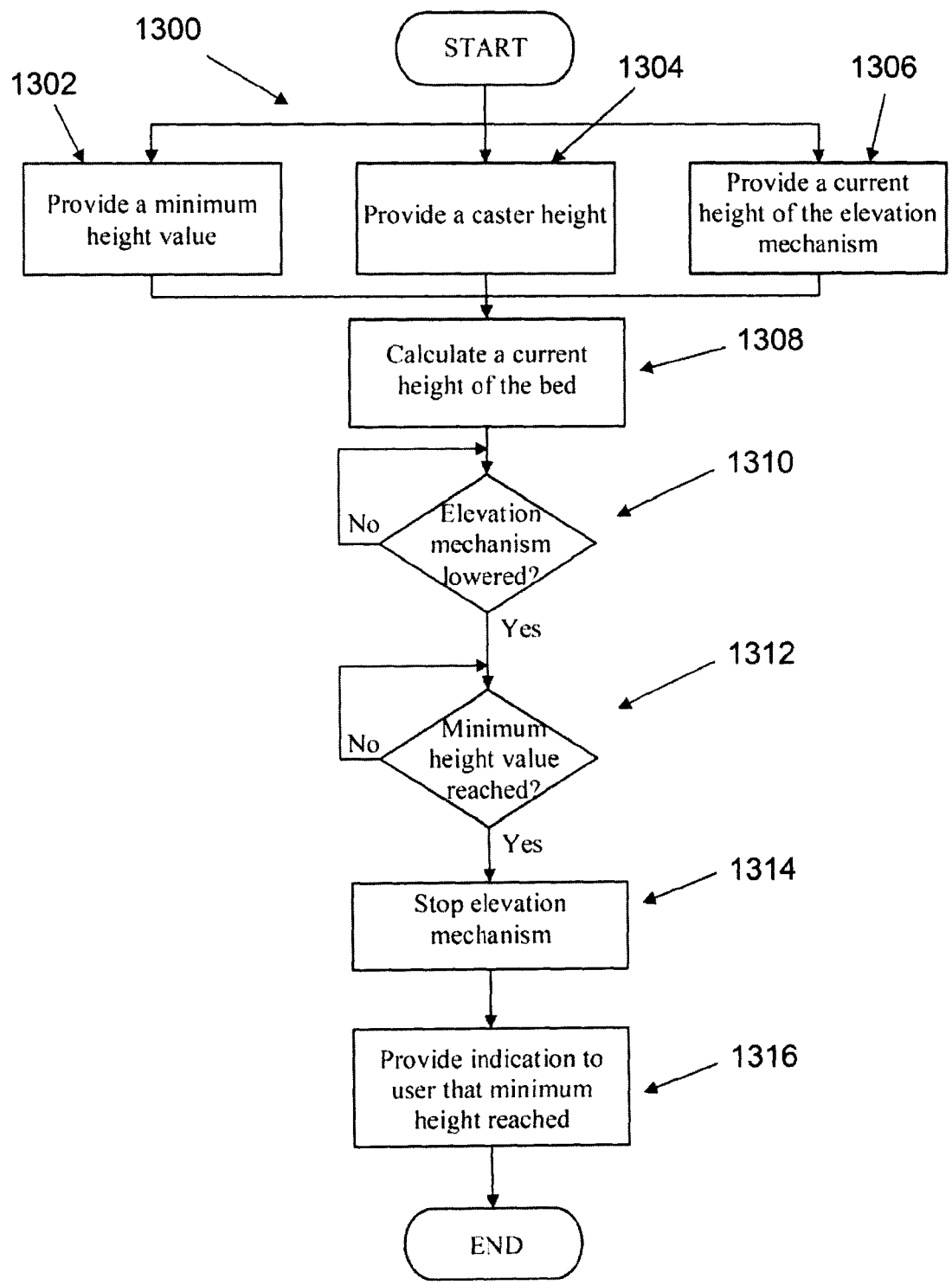
FIG. 13 is a flowchart of a method for limiting the height of the hospital bed illustrated in FIG. 12.

Now turning to FIG. 13, there is shown a method 1300 for limiting the height of the hospital bed 1202, in accordance with one embodiment. As explained above, the height of the hospital bed 1202 corresponds to the height of the patient receiving surface 1206 relative to the ground surface.

According to 1302, the minimum height value is first provided by the user. Specifically, the minimum height value may be provided into the memory 1258 via the user interface 1256.

Figure 14:
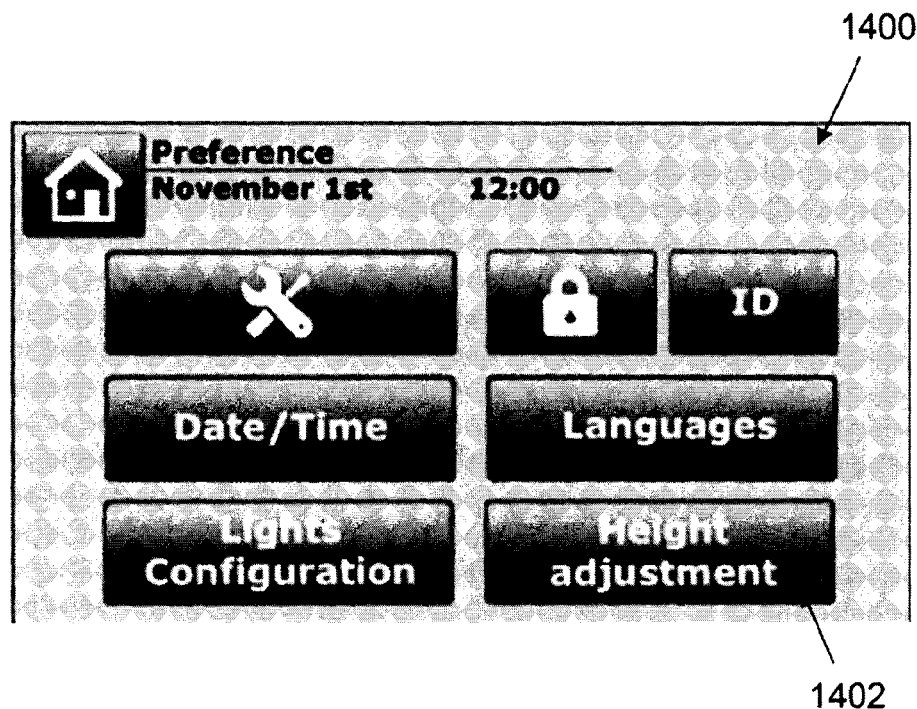
FIG. 14 is a diagram of a touchscreen for the hospital bed system illustrated in FIG. 12, displaying a preference image which includes a height configuration button.

FIG. 14 shows a preference image 1400 displayed on the display. The preference image 1400 includes a height configuration button 1402 which may be activated by the user to provide the minimum height value or to modify the minimum height value currently entered or selected in the memory 1258. In one embodiment, the activation of the height configuration button 1402 is password-protected such that a corresponding password must be inputted in order to activate the height configuration button 1402.

Figure 15:
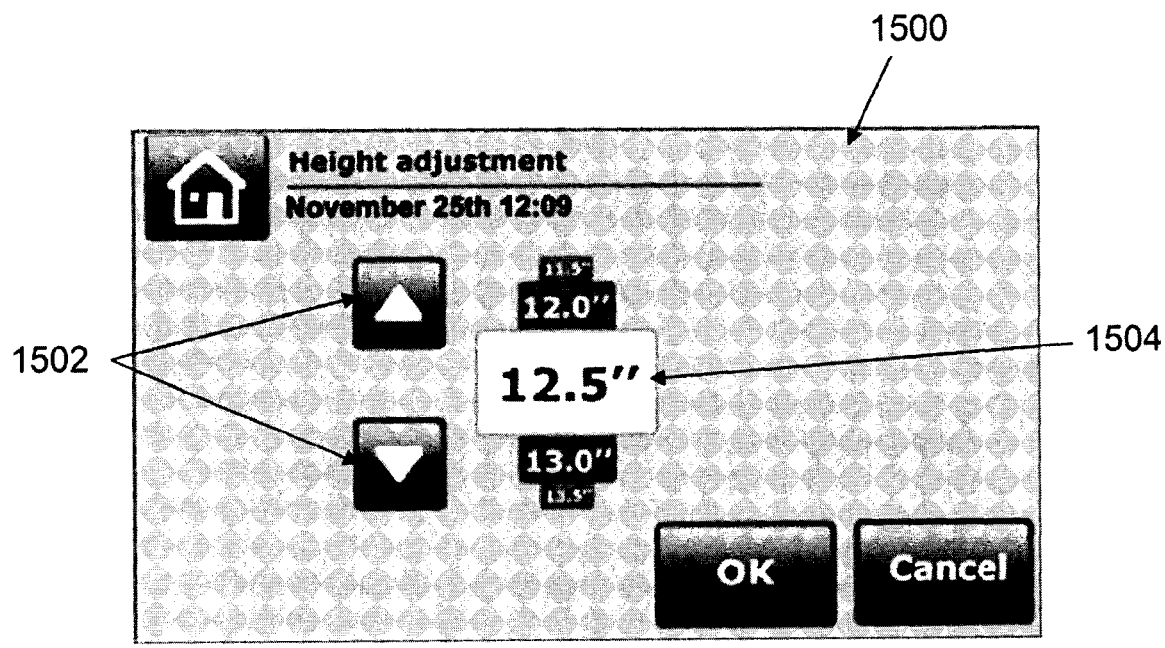
FIG. 15 is another diagram of the touchscreen for the hospital bed system illustrated in FIG. 12, displaying a minimum height adjustment image which allows a user to select one of a plurality of predetermined minimum height values.

In the illustrated embodiment, activating the height configuration button 1402 causes the display 1260 to display a minimum height adjustment image 1500 as shown in FIG. 15. Still in the illustrated embodiment, the minimum height adjustment image 1500 includes a pair of scrolling buttons 1502 which can be activated by the user to cycle through a plurality of predetermined minimum height values 1504 provided from the memory 1258, in order to select one of the predetermined minimum height values. In one embodiment, the predetermined minimum height values range from 10 inches to 16 inches when the casters 1208 of the bed 1202 include dual casters, and from 11½ inches to 17½ inches when the casters 1208 include single casters. Alternatively, the user could instead manually enter a desired minimum height value into the memory 1258 via the user interface 1256.

Referring back to FIG. 13, according to 1304, the caster height or wheel size is further provided, as explained above.

According to 1306, an indication of the current height of the elevation mechanism 1210 is further provided by the height sensor 1252 to the processing unit 1254.

According to 1308, the current height of the bed 1202 is then computed or calculated by the processing unit 1254 based on the caster height and the indication from the height sensor 1252.

According to 1310, vertical movement of the elevation mechanism 1210 is then monitored. Specifically, if the elevation mechanism 1210 is lowered such that the patient support surface 1206 moves towards the ground surface, an indication that the elevation mechanism 1210 is moving downwardly is received by the processing unit 1254 from the elevation mechanism 1210.

According to 1312, upon receiving an indication that the patient receiving surface 1206 is moving downwardly, the processing unit 1254 compares the calculated current height with the selected minimum height value. If the current height is equal to the selected minimum height value, the processing unit 1254 stops the elevation mechanism 1210 and prevents the elevation mechanism 1210 from further moving downwardly, in accordance with 1314.

According to 1316, the processing unit 1254 further provides an indication to the user that the selected minimum height value has been reached. For example, the indication could include a visual indicator, such as text, provided on the display 1260 to indicate to the user that the selected minimum height value has been reached.

It will be appreciated that this height limiting system 1250 may help preventing damage to medical equipment, cables or other objects which may be stored under the patient support surface. The height limiting system 1250 may also advantageously allow the minimum height value to be changed and adjusted according to the size of the items stored under the bed, or to the configuration of the room and of the ground surface below the bed.

We claim:

1. A bed comprising:
    a frame;
    a patient receiving surface for receiving a patient thereon, the patient receiving surface being supported by the frame,
    an elevation mechanism secured to the frame and to the patient receiving surface for moving the patient receiving surface vertically relative to a ground surface on which the bed is placed;
    a bed height limiting system for limiting a height of the patient receiving surface to a minimum height relative to the ground surface, the bed height limiting system comprising:
        a height sensor;
        a processing unit operatively connected to the elevation mechanism and the height sensor; and
        a user interface operatively connected to the processing unit,
    wherein the processing unit is operable to:
        receive an indication of a minimum height provided by a user via the user interface;
        receive, from the height sensor, an indication of a current elevation mechanism height;
        determine, based on the indication of the current elevation mechanism height, a current bed height; and
        in response to the current bed height being equal to the minimum height:
            provide a stop command to the elevation mechanism to stop a downward movement of the elevation mechanism.

2. The bed of claim 1, wherein the processing unit is further operable to, prior to the providing of the stop command to the elevation mechanism:
    receive an indication of the downward movement of the elevation mechanism.

3. The bed of claim 1, where in the processing unit is further operable to:
    provide, to the user interface, an indication that the minimum height has been reached.

4. The bed of claim 1, wherein the elevation mechanism is located under the frame.

5. The bed of claim 1, wherein the bed height limiting system further comprises a memory operatively connected to the processing unit for storing the minimum height.

6. The bed of claim 1, wherein the elevation mechanism comprises a front elevation assembly located near a front end of the bed and a rear elevation assembly located near a rear end of the bed.

7. The bed of claim 6, wherein each one of the front and rear elevation assembly comprises at least one actuator.

8. The bed of claim 7, wherein the height sensor is operatively connected to the at least one actuator of the elevation mechanism.

9. The bed of claim 8, wherein the at least one actuator comprises a linear actuator.

10. The bed of claim 8, wherein the processing unit is operable to, prior to the determining the current height of the bed:
    receive the indication of the current elevation mechanism height comprising a measurement of extension of each one of the at least one actuator, the measurement of extension corresponding to a length by which the at least one actuator is extended; and
    calculate, based on the measurements of extension, a height between a bottom end and a top end of the front and rear elevation assemblies of the elevation mechanism to obtain the current height of the elevation mechanism.

11. The bed of claim 1, wherein the frame is mounted on a plurality of casters.

12. The bed of claim 11, wherein the processing unit is operable to determine the current bed height based on the current elevation mechanism height and a height of the plurality of casters.

13. The bed of claim 12, wherein the height sensor comprises an optical sensor.

14. The bed of claim 1, further comprising a display operatively connected to the processing unit for displaying data related to the bed to the user.

15. The bed of claim 14, wherein at least one of the user interface and the display comprises a touchscreen.

16. The bed of claim 14, wherein the touchscreen is configured to display data to the user and to allow the user to input commands to the processing unit and to provide parameters into a memory operatively connected to the processing unit.

17. A bed height limiting system for limiting a height of a hospital bed, the hospital bed comprising: a frame, a patient receiving surface supported by the frame, the patient receiving surface and the frame being secured to an elevation mechanism, the elevation mechanism being operable to move the patient receiving surface relative to a ground surface, the bed height limiting system comprising:
    a processing unit operatively connected to the elevation mechanism; and
    a memory operatively connected to the processing unit, the memory storing a predetermined height;
    the processing unit being operable to:
        receive an indication of a current height of the patient receiving surface;
        receive, from the elevation mechanism, an indication of a downward movement of the patient receiving surface;
        in response to the receiving the indication of the downward movement of the patient receiving surface:
            receive the predetermined height from the memory;
            compare the current height with the predetermined height; and
            in response to the current height of the patient receiving surface being equal to the predetermined height:
                cause the elevation mechanism to stop further downward movement.

18. The bed height limiting system of claim 17, further comprising
    a height sensor operatively connected to the elevation mechanism; and wherein
    to receive the indication of the current height of the patient receiving surface, the processing unit is operable to:

receive an indication of the current elevation mechanism height from the height sensor; and determine, based on the current elevation mechanism height, the current height of the patient receiving surface.

19. The bed height limiting system of claim 18, wherein the memory stores a caster height; and wherein to determine, based on the current elevation mechanism height, the current height of the patient receiving surface, the processing unit is operable to:

receive the caster height; and add the caster height to the current elevation mechanism height.

20. The bed height limiting system of claim 19, wherein the processing unit is further operable to:

provide, to a display interface connected to the processing unit, an indication that the predetermined height has been reached.

\* \* \* \* \*